Figure 1:
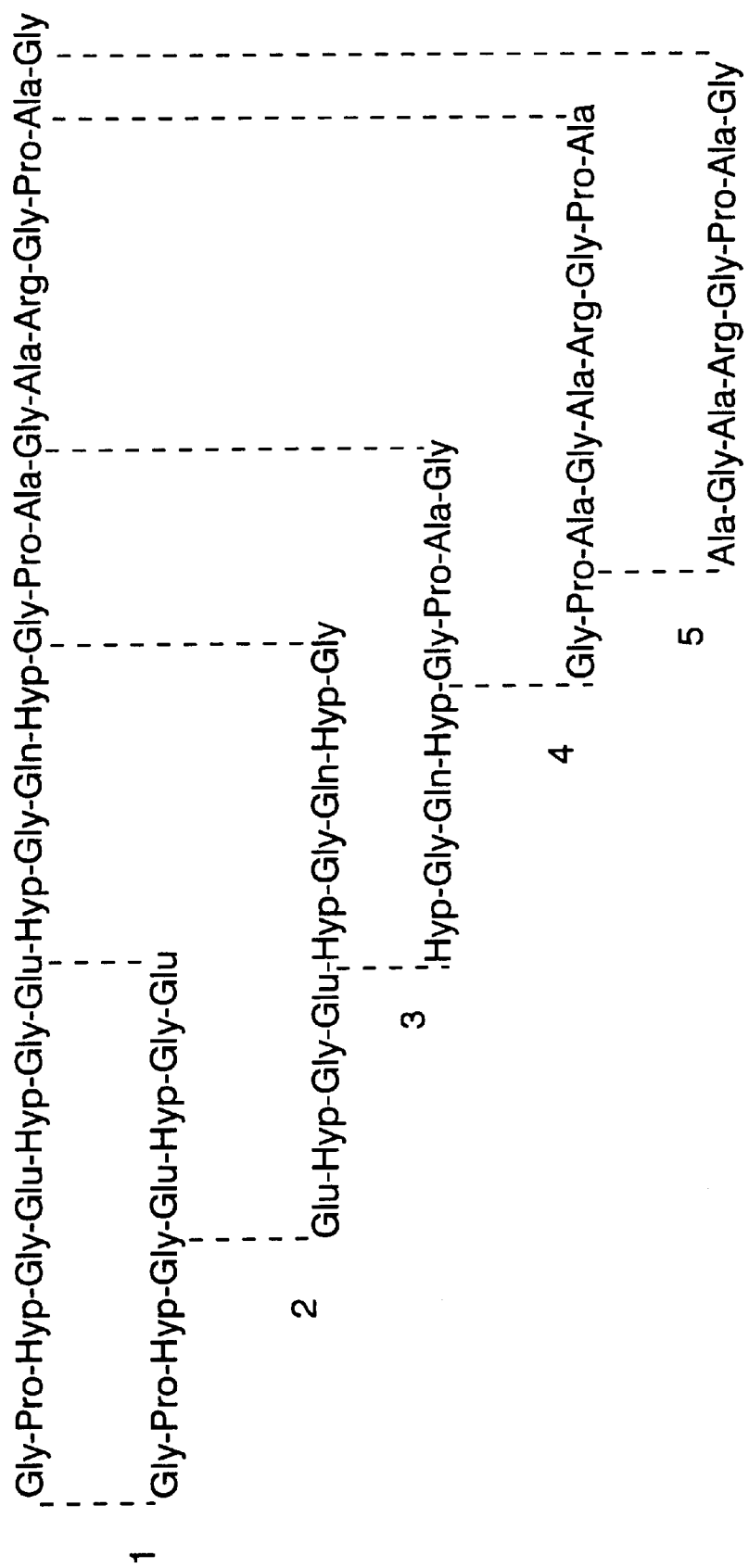

United States Patent [19]

Broadley et al.

[11] Patent Number: 6,096,864

[45] Date of Patent: Aug. 1, 2000

[54] PEPTIDES FOR USE IN WOUND TREATMENT

[75] Inventors: Kenneth Broadley, Nass, Ireland; Christine Hamilton, Ealing, United Kingdom

[73] Assignee: Johnson & Johnson Medical, Ltd., Edinburgh, United Kingdom

[21] Appl. No.: 09/007,555

[22] Filed: Jan. 15, 1998

[51] Int. Cl.[7] .............................. A61K 38/04; C07K 5/00
[52] U.S. Cl. ...................... 530/330; 530/328; 530/329; 514/15; 514/16; 514/17
[58] Field of Search .................................. 530/331, 328, 530/329, 330; 514/17, 18, 16, 15

[56] References Cited

U.S. PATENT DOCUMENTS 5,235,038  8/1993  Blondelle et al. ................. 514/12
5,591,711  1/1997  Koyama et al. .................... 514/6

FOREIGN PATENT DOCUMENTS

WO 90/00569  1/1990  European Pat. Off. .

OTHER PUBLICATIONS

WPI Abstract Accession No. 84–235498/38 & RO 0083934 A Radulescu et al. May, 5, 1984 (see abstract).
A.E. Postlethwaite et al. in *Proceedings of National Academy of Science*, vol. 75, pp. 871–875 (1978).
Sato, et al., Bull. Chen. Soc. Jpn. 1983, 56, 1657.

*Primary Examiner*—Cecilia J. Tsang
*Assistant Examiner*—Fabian A. Jameison
*Attorney, Agent, or Firm*—Andrew C. Farmer; Theodore J. Shatynski

[57] ABSTRACT

The invention provides wound treatment compositions comprising from $10^{-6}$% to 1.0% w/w of one or more peptides, wherein the peptides are from 3 to 30 amino acid residues long and comprise the sequence Gly-Pro-Ala. Preferably, the peptides comprise the sequence Gly-Pro-Ala-Gly, more preferably at the N-terminus. The peptides exhibit a chemotactic effect towards fibroblasts.

11 Claims, 3 Drawing Sheets

```
                        SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
         (A) LENGTH: 22 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 3
         (D) OTHER INFORMATION: /product= "Hyp"

(ix) FEATURE:
         (A) NAME/KEY: Modified-site
         (B) LOCATION: 6
         (D) OTHER INFORMATION: /product= "Hyp"

(ix) FEATURE:
         (A) NAME/KEY: Modified-site
         (B) LOCATION: 9
         (D) OTHER INFORMATION: /product= "Hyp"

(ix) FEATURE:
         (A) NAME/KEY: Modified-site
         (B) LOCATION: 12
         (D) OTHER INFORMATION: /product= "Hyp"
```

(xi) SEQUENCE DESCRIPTION: SEQ ID NO:1:

Gly Pro Xaa Gly Glu Xaa Gly Glu Xaa Gly Gln Xaa Gly Pro Ala Gly
1               5                  10                  15

Ala Arg Gly Pro Ala Gly
            20

(2) INFORMATION FOR SEQ ID NO:2:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 3
        (D) OTHER INFORMATION: /product= "Hyp"

(ix) FEATURE:
        (A) NAME/KEY: Modified-site
        (B) LOCATION: 6
        (D) OTHER INFORMATION: /product= "Hyp"

(xi) SEQUENCE DESCRIPTION: SEQ ID NO:2:

Gly Pro Xaa Gly Glu Xaa Gly Glu
1               5

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /product= "Hyp"

(ix) FEATURE:
        (A) NAME/KEY: Modified-site
        (B) LOCATION: 5
        (D) OTHER INFORMATION: /product= "Hyp"

(ix) FEATURE:
        (A) NAME/KEY: Modified-site
        (B) LOCATION: 8
        (D) OTHER INFORMATION: /product= "Hyp"

(xi) SEQUENCE DESCRIPTION: SEQ ID NO:3:

Glu Xaa Gly Glu Xaa Gly Gln Xaa Gly
1               5

(2) INFORMATION FOR SEQ ID NO:4:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site (B) LOCATION: 1
          (D) OTHER INFORMATION: /product= "Hyp"

(ix) FEATURE:
          (A) NAME/KEY: Modified-site
          (B) LOCATION: 4
          (D) OTHER INFORMATION: /product= "Hyp"

(xi) SEQUENCE DESCRIPTION: SEQ ID NO:4:

Xaa Gly Gln Xaa Gly Pro Ala Gly
1               5

(2) INFORMATION FOR SEQ ID NO:5:

(i) SEQUENCE CHARACTERISTICS:
         (A) LENGTH: 9 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:5:

Gly Pro Ala Gly Ala Arg Gly Pro Ala
1               5

(2) INFORMATION FOR SEQ ID NO:6:

(i) SEQUENCE CHARACTERISTICS:
         (A) LENGTH: 8 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:6:

Ala Gly Ala Arg Gly Pro Ala Gly
1               5

(2) INFORMATION FOR SEQ ID NO:7:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:7:

Gly Pro Ala Gly Ala
1               5

(2) INFORMATION FOR SEQ ID NO:8:

(i) SEQUENCE CHARACTERISTICS:
         (A) LENGTH: 6 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:8:

Gly Pro Ala Gly Ala Arg
1               5

(2) INFORMATION FOR SEQ ID NO:9:

```
    (i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Gly Pro Ala Gly Ala Arg Gly
1               5

(2) INFORMATION FOR SEQ ID NO:10:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Gly Pro Ala Gly Ala Arg Gly Pro
1               5
```

PEPTIDES FOR USE IN WOUND TREATMENT

The present invention relates to the use of certain peptides in the treatment of wounds.

Wound healing involves a complex series of interactions between many cell types and between cells and their extracellular matrix (ECM). Many cell types, cytokines, coagulation factors, growth factors and complement activation and mat-ix proteins such as fibronectin and collagen contribute to healing in various proportions. The functions and precise mechanisms of the cellular, humoral and local factors are unclear and poorly understood.

It is known that wound dressings comprising collagen can have a positive Therapeutic effect on wound healing. It has been shown that collagen is chemotactic towards a variety of cell types, including neutrophils, monocytes, and fibroblasts. The cheinotaxis is thought to be advantageous for wound healing.

A. E. Postlethwaite et al. in *Proceedings of the National Academy of Science*, Volume 75, Pages 871–875 (1978) describe studies on the chemotactic attraction of human fibroblast to type I, II and III collagen and collagen-derived peptides. Three peptides (Gly-Hyp, Gly-Pro-Hyp and Pro-Hyp) obtained by collagen digestion with bacterial collagenase were chemotactic for fibroblasts, but only in the range of 2.5 mM to 25 mM. According to Postlethwaite et al., the peptide Gly-Pro-Ala was found to have no chemotactic activity in the same concentration range.

It is an object of the present invention to identify further collagen-derived peptides that are chemotactic towards wound healing cells, in particular fibroblasts.

It is a further object of the present invention to identify peptides that are chemotactic at much lower concentrations than those known in the art.

The present invention provides a wound treatment composition comprising from $10^{-6}$ to 1.0% w/w of one or more peptides, said peptides being from 3 to 20 amino acid residues long and comprising the sequence Gly-Pro-Ala.

Preferably, the peptides are from 4 to 20 amino acid residues long and comprise the sequence Gly-Pro-Ala-Gly. More preferably, the peptides are from 4 to 12 amino acid residues long. Preferably, the Gly-Pro-Ala or Gly-Pro-Ala-Gly sequences are at the N-terminus of the peptide.

Most preferably, the peptides are selected from the group consisting of Gly-Pro-Ala-Gly and Gly-Pro-Ala-Gly-Ala-Arg-Gly-Pro-Ala (SEQ ID NO, 5).

Preferably, the composition comprises from $10^{-4}$ to 1.0% w/w (0.001 to 10 mg/ml) more preferably $10^{-3}$ to 1.0% w/w and most preferably $10^{-3}$ to 0.1% w/w of the one or more peptides. Most preferably, the composition comprises about 0.01% w/w or 0.1 mg/ml of the one or more peptides.

In certain preferred embodiments the wound treatment composition according to the present invention is a liquid, gel or semi-solid ointment for topical application to a wound comprising the one or more peptides in a pharmaceutically acceptable carrier. Suitable carriers include: hydrogels containing cellulose derivatives, including hydroxyethyl cellulose, hydroxymethyl cellulose, carboxymethyl cellulose, hydroxypropylmethyl cellulose and mixtures thereof; and hydrogels containing polyacrylic acid (Carbopols). Suitable carriers also including creams/ointments used for topical pharmaceutical preparations, e.g. creams based on cetomacrogol emulsifying ointment. The above carriers may include alginate (as a thickener or stimulant), preservatives such as benzyl alcohol, buffers to control pH such as disodium hydrogen phosphate/sodium dihydrogen phosphate, agents to adjust osmolarity such as sodium chloride, ad stabilisers such as EDTA.

In other preferred embodiments, the wound treatment composition is coated onto, or incorporated into a solid wound dressing such as a film, a fibrous pad or a sponge. The solid dressing may be bioabsorbable, whereby slow release of the chemotactic peptides is achieved. The peptides may be simply coated onto the solid dressing by dipping, or may be covalently bound to, or may be dispersed therein as a solid solution. Suitable solid wound dressings include the absorbent polyurethane foam available under the Registered Trade Mark TIELLE (Johnson & Johnson Medical, Inc.), fibrous alginate pads such as those available under the Registered Trade Mark KALTOSTAT (Convatec Corporation), and bioabsorbable collagen/alginate materials available under the Registered Trade Mark FIBRACOL (Johnson & Johnson Medical, Inc.).

The present invention also provides the use of one or more peptides as hereinbefore defined having from 3–20 amino acids and comprising the N-terminal sequence Gly-Pro-Ala for the preparation of a composition for wound treatment.

In another aspect, the present invention provides a method for the treatment of wounds comprising the step of applying to the surface of a wound a wound treatment composition according to the present invention.

Figure 2:
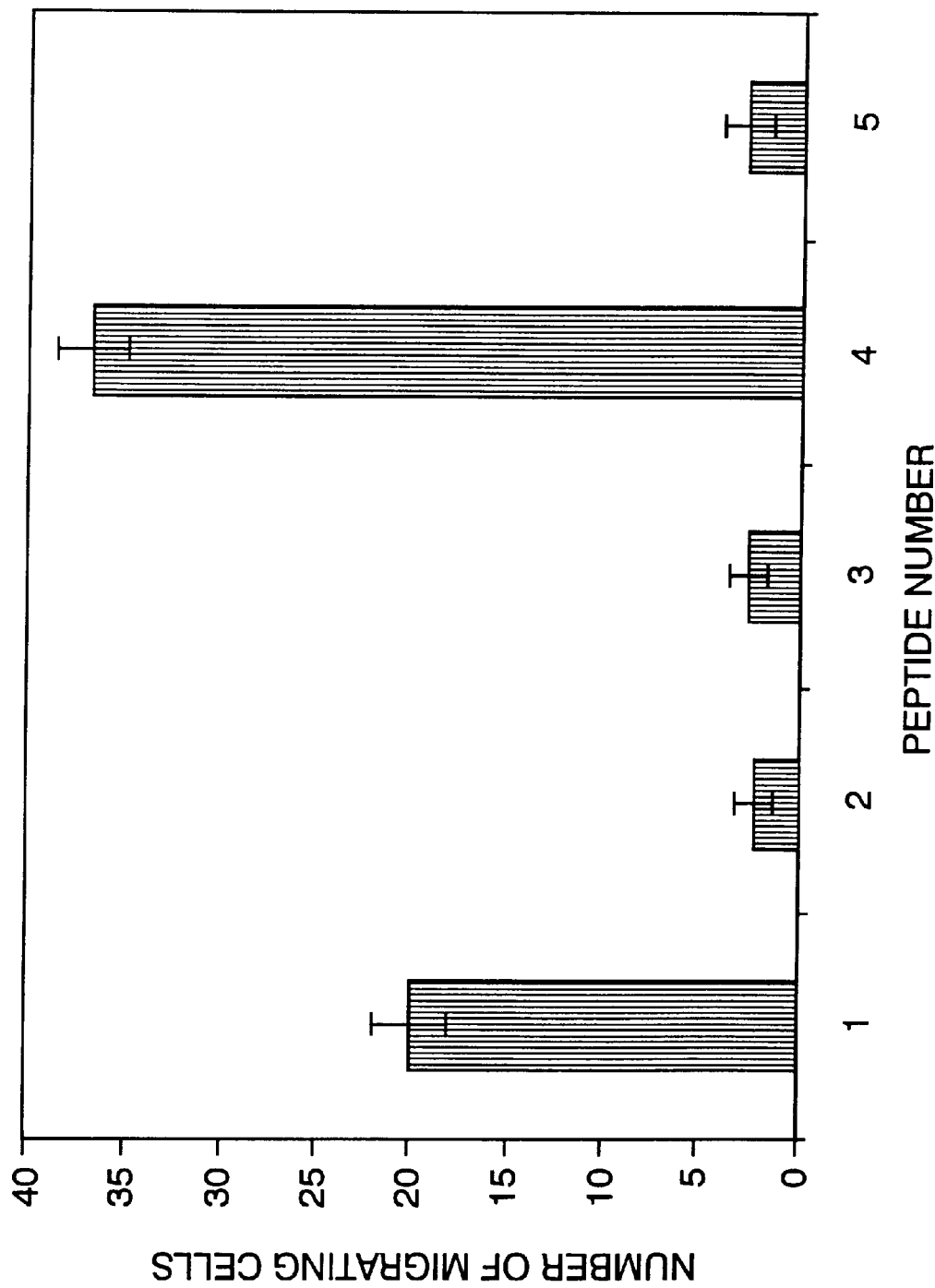
Figure 3:
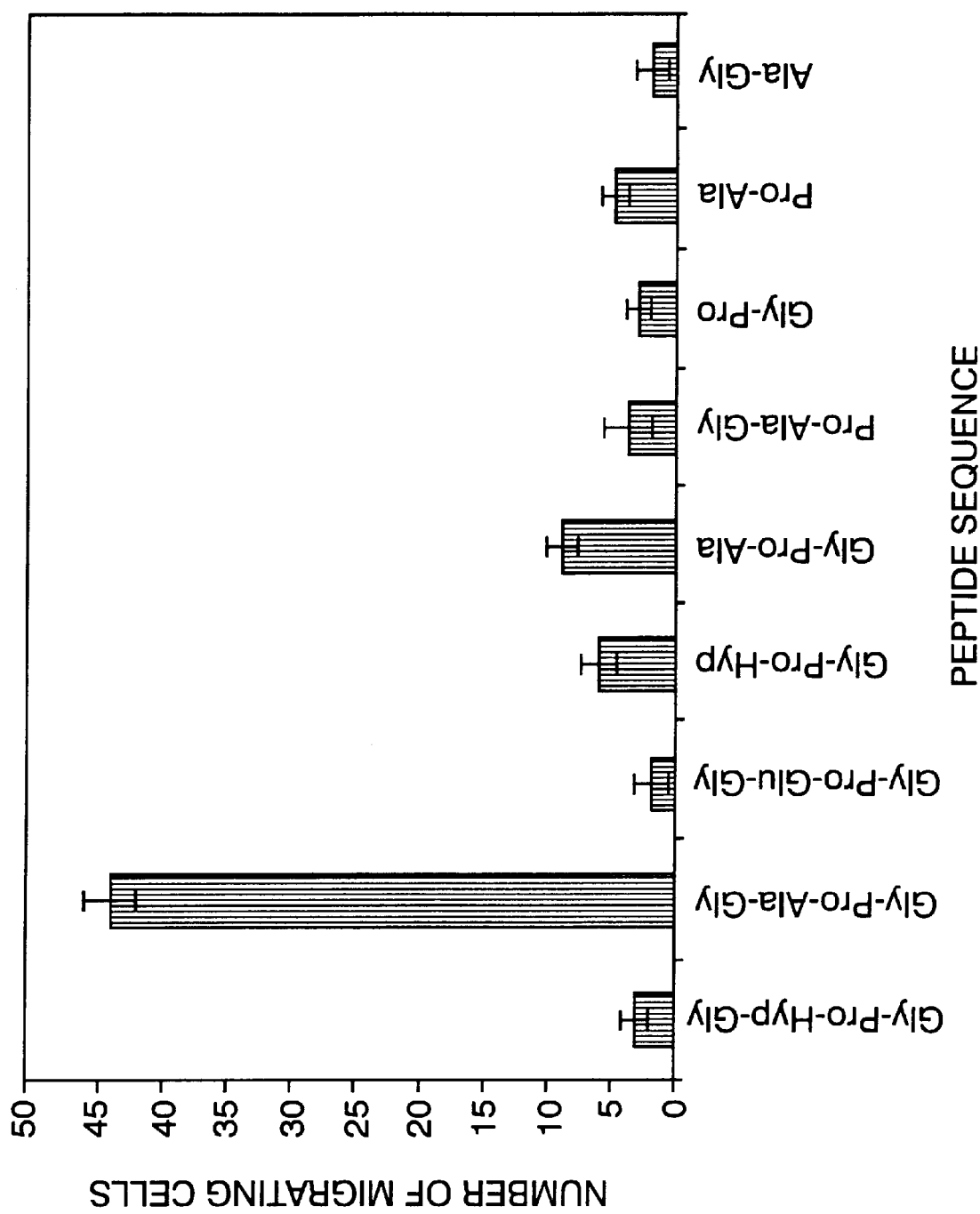

Specific embodiments of the present invention will now be described further, with reference to the accompanying drawings, in which:

FIG. 1 shows an active 22 amino acid obtained from a collagen digest together with 5 synthetic peptides designed to locate the active region of the 22 amino acid peptides;

FIG. 2 shows the chemotactic activity (as number of migrating cells) of the 5 synthetic peptides of FIG. 1; and FIG. 3 shows the chemotactic activity (as number of migrating cells) of a series of shorter synthetic peptides.

The chemotactic peptides used in the present invention were identified as follows.

Type I collagen was prepared from pig skin by pepsin digestion and selective salt precipitation, as described by E. J. Miller et al. in *Methods in Enzymology*, Volume 83, Page 33 (1982). Samples were dissolved in 50 mM tris-HCl pH 7.5 containing 0.15M NaCla, 5mM $CaCl_2$, 10 mM NEM [what is this?] and incubated for 24 hours at 37° C. with bacterial collagenase from Clostridium Haemoliticus (Sigma Chemical Co.) at a ratio of 1:100 w/w enzyme:collagen. Chymotrypsin (Sigma Chemical Co.) was then added at an enzyme:collagen ratio of 1:100 w/w, and the resulting digest was incubated for 24 hours at 37° C.

The crude digest was then fractionated by HPLC. The corrected fractions were then tested individually as described below for chemotactic activity towards fibroblasts. Fraction No. 4 of the HPLC separation contained the majority of the chemotactic activity of the whole digest. From within this fraction individual peptides were isolated and tested for their potential to induce chemotaxis. A peptide was identified which contained the greatest chemotactic properties within this fraction. The amino acid sequence of the peptide showed it to be residues 25–46 of the α2(I) chain of type I collagen, as shown in FIG. 1. This peptide was synthesised and assayed for its ability to induce fibroblast chemotaxis. It was found that the synthetic peptide induced fibroblast chemotaxis with maximum activity at a peptide concentration of about 0.1 mg/ml.

In order to determine the part of the 22 amino acid peptide responsible for the chemotactic activity, synthetic collagen peptides were created which contained regions of the 22 amino acid sequence. Five peptides, each of eight or nine amino acids in length, were synthesised as shown in FIG. 1. The amino acid sequences of the synthesised peptides contained regions of overlap. The five peptides were then tested for their ability to stimulate fibroblast chemotaxis, using them as described below, at a concentration 0.1 mg/ml. Peptide sequence 4 stimulated chemotaxis to the greatest extent, as shown in FIG. 2.

From the sequences of these peptides, another batch of smaller collagen peptides having from 2 to 4 amino acid residues were synthesised and tested similarly for chemotactic activity towards the fibroblasts. The results are shown in FIG. 3. From these and other experiments, it was concluded that peptides having Gly-Pro-Ala, and especially Gly-Pro-Ala-Gly at the N-terminus are especially chemotactic towards fibroblasts in this concentration range.

The chemotactic effect is known to correlate strongly with the promotion of wound healing in mammals.

EXAMPLE 1

A wound treatment composition in accordance with the present invention was prepared as follows.

First, the active peptide Gly-Pro-Ala-Gly was synthesised in a fully automated applied biosystems 430A peptide synthesiser. The Fmoc/tBu based method of peptide synthesis was used which involves the use of the base labile 9-fluorenylmethoxycarbonyl amino protecting group in conjunction with acid labile side protection and peptide-resin linkage. The peptide was synthesised using Fmoc-Glycine functionalised 4-alkoxybenzylalcohol resin (Wang Corporation), and all amino acids were incorporated using double coupling cycles. Each synthetic cycle involved: (1) treatment with acetic anhydride to cap any free amino groups prior to amine deprotection, (2) Fmoc removal by treatment with the organic base piperidine, and (3) coupling of the next amino acid in the sequence. In this way the desired peptide was built up from the C to N terminus. The peptide was then cleaved from the resin with simultaneous removal of side chain protecting groups by treatment with a mixture of TFA/ethanedithiol/triisopropylsilane/thioanisole and water for 3 hours at room temperature. The resin was then removed by filtration, the TFA evaporated and the peptide isolated by precipitation with diethyl ether and filtration. The crude peptide was then purified by reverse phase HPLC and lyophilised. Laser desorption mass spectrum and analytical HPLC were carried out to confirm purity of the peptide.

The purified peptide was incorporated by mixing into a wound ointment having the following composition:

| | |
|---|---|
| Carboxymethyl cellulose | 2.4% |
| Hydroxyethyl cellulose | 0.3% |
| Sodium chloride | 0.24% |
| Propylene glycol | 20% |
| N-acetyl cysteine | 0.01% |
| Water | 100% |

The resulting ointment is a clear gel suitable for application to the surface of a wound.

The above embodiment has been described by way of example only. Many other embodiments falling within the scope of the accompanying claims will be apparent to the skilled reader.

We claim:

1. A wound treatment composition comprising $10^{-6}\%$ to 1% w/w of a tetrapeptide, said tetrapeptide is of the formula Gly-Pro-Ala-x, wherein x is an amino acid residue.

2. The composition of claim 1, wherein x is GLY.

3. A wound treatment composition comprising $10^{-6}\%$ to 1% w/w of the peptide Gly-Pro-Ala-Gly-Ala (SEQ ID NO: 7).

4. A wound treatment composition comprising $10^{-6}\%$ to 1% w/w of the peptide Gly-Pro-Ala-Gly-Ala-Arg (SEQ ID NO: 8).

5. A wound treatment composition comprising $10^{-6}\%$ to 1% w/w of the peptide Gly-Pro-Ala-Gly-Ala-Arg-Gly (SEQ ID NO: 9).

6. A wound treatment composition comprising $10^{-6}\%$ to 1% w/w of the peptide Gly-Pro-Ala-Gly-Ala-Arg-Gly-Pro (SEQ ID NO: 10).

7. A wound treatment composition comprising $10^{-6}\%$ to 1% w/w of the peptide Gly-Pro-Ala-Gly-Ala-Arg-Gly-Pro-Ala (SEQ ID NO: 5).

8. The composition of any of the claims 1–7, wherein the composition comprises $10^{-4}\%$ to 0.1% w/w of said one or more peptides.

9. The composition of any of the claims 1–7, wherein the composition is an ointment for topical application to a wound.

10. A solid wound dressing for application to a wound, said dressing having the wound treatment composition of any of the claims 1–7.

11. A method of treating a wound comprising the step of applying a therapeutically effective amount of a wound treatment composition comprising the wound treatment compositions of any of the claims 1–7.

* * * * *